United States Patent

Mountain et al.

[11] Patent Number: 6,064,480
[45] Date of Patent: May 16, 2000

[54] METHOD OF OPTICAL PARTICLE COUNTING FOR WATER MIXED LUBRICANT

[75] Inventors: John W. Mountain, Harriman; Mong Ching Lin, Knoxville; A. Andrew Carey, Lenoir City, all of Tenn.

[73] Assignee: CSI Technology, Inc., Wilmington, Del.

[21] Appl. No.: 09/032,139

[22] Filed: Feb. 27, 1998

[51] Int. Cl.⁷ .................................................. G01N 15/02
[52] U.S. Cl. .......................... 356/335; 356/330; 356/335; 356/337
[58] Field of Search .................... 356/330, 335, 356/337

[56] References Cited

U.S. PATENT DOCUMENTS

| | | | |
|---|---|---|---|
| 3,892,485 | 7/1975 | Merritt et al. | 356/103 |
| 4,003,661 | 1/1977 | Yamano | 356/201 |
| 4,790,650 | 12/1988 | Keady | 356/37 |
| 4,857,829 | 8/1989 | Sagae et al. | 324/61 |

*Primary Examiner*—Robert H. Kim
*Assistant Examiner*—Reginald A. Ratliff
*Attorney, Agent, or Firm*—Luedeka, Neely & Graham, PC

[57] ABSTRACT

Solid particles combined with a water contaminated oil sample are counted by an optical particle counter. The contaminated oil sample is mixed at a substantially 1:1 ratio with a water masking solvent comprising about one part isopropanol and about three parts toluene. The oil and solvent mixture is passed through a transparent viewing volume between a light source and a light detector for detection and counting of oil suspended solid particles.

24 Claims, 2 Drawing Sheets

METHOD OF OPTICAL PARTICLE COUNTING FOR WATER MIXED LUBRICANT

BACKGROUND OF THE INVENTION

The present invention relates, generally, to methods for analyzing lubrication oil. More particularly, the invention relates to the preparation of oil test specimens for analytical processing by an optical particle counter.

Notwithstanding the traditional perception that water and oil do not mix, in fact, water may mix with oil by three distinct mechanisms: 1) by free droplet dispersion; 2) by emulsion; and 3) by solution. At room temperature, the solubility of water in a transformer (paraffinic) type oil is about 20 ppm. The room temperature solubility of water in an aromatic (napthenic) oil is about 200 ppm.

For every 25° C. temperature increase, the solubility of water in oil approximately doubles. Additionally, certain oil additives may increase the water solubility therein. Although dissolved water in a lubrication system is relatively benign, a water concentration held in dissolved dispersion at a higher temperature or chemical equilibrium may be at least partially precipitated in situ to free water by cooling or chemical change.

The presence of dispersed free water is often revealed by a hazy or cloudy appearance to the fluid. A confident but only qualitative confirmation of free water in oil is provided by a "crackle test". Free water mixed with oil "crackles" when heated above the water boiling point. The Karl Fischer reagent method, specified by ASTM D-1744, is the industry standard for quantatively measuring the presence of water in oil to an accuracy of about 10 ppm.

One of the more reliable methods for analytically determining the degree of solid particle contamination of a lubrication fluid is by means of an optical particle counter. Operatively, an optical particle counter is constructed to flow an oil specimen through a thin, transparent segment of fluid flow channel. A light source on one side of the transparent segment issues a light beam through the specimen as it flows through the transparent channel segment. On the opposite side of the transparent segment of flow channel, the light emerging from the specimen flow stream falls upon a light detector means such as a photodiode. The light detector generates signals corresponding to the size and frequency of solid particles passing through the transparent segment of flow channel while in suspension with such oil as a consequence of blocking of the light path between the light source and light detector.

When an oil specimen is also contaminated with dispersed free water, the water is distributed throughout the specimen as free droplets or as globules of emulsion. The light refractive index of these droplets or globules differs from that of the remaining fluid body. Hence, the water droplet or globule passing through the transparent segment of flow channel either blocks or disperses the light beam resulting in a report by the light detector as the passing of a solid particle. This false solid particle report vitiates the integrity of the solid particle count data.

It is, therefore, an object of the present invention to distinguish true solid particles counted by an optical particle counter from water particles.

Another object of the present invention is to mask free water in a contaminated oil specimen to an optical particle counter.

A further object of the present invention is a test sample preparation method for optical particle counters that masks free water sites in a contaminated oil specimen.

SUMMARY OF THE INVENTION

These and other objects of the invention are accomplished with an optical particle counting instrument having a transparent area across a test sample flow conduit. Aligned with the transparent area on respectively opposite sides of the flow conduit is a light emitter and a light detector. The light detector generates an electrical signal responsive to the passage of a light obstructing particle between the light emitter and the light detector. Signals generated by the light detector are processed to count the particle passage event and in some cases, evaluate and categorize the size of the passing particle.

A test sample for oil that is contaminated with both water and solid particles is prepared for a particle count analysis by dilution with a water masking solvent. The masking solvent comprises a weight measured mixture of about one part isopropanol and about three parts toluene. The masking solvent is thoroughly mixed with a contaminated oil specimen at a weight ratio of about 1:1. A known weight, volume or flow rate of the diluted test sample is passed through the particle counting instrument flow conduit. The resulting test sample has a substantially homogeneous refractive index thereby isolating the solid particle contaminates of the oil constituency from the water contamination.

BRIEF DESCRIPTION OF THE DRAWINGS

The invention will be better understood and appreciated, along with the aforedescribed objects and features thereof, from the following detailed description of the preferred embodiment when considered in conjunction with the drawings in which.

DESCRIPTION OF THE PREFERRED EMBODIMENTS

Figure 1:
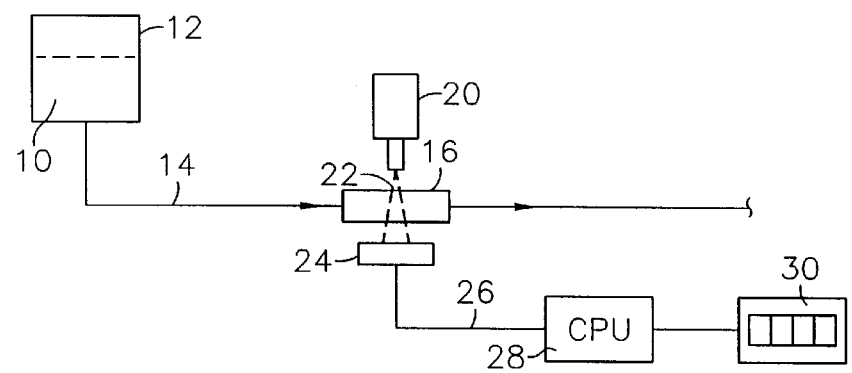
FIG. 1 is a general schematic of an optical particle counter.

Referring to FIG. 1 of the drawings, an abbreviated schematic of an optical particle counter is represented to include a specimen vessel 12 connected to a fluid flow conduit 14. The conduit 14 channels a volume of fluid test specimen 10 through a transparent conduit sector 16. Transparent conduit sectors may also be characterized as "windows" or as "view volume areas". Usually, some means is used or procedure followed to control and thereby determine the quantity of test specimen 10 delivered through the transparent sector 16, either as a known volume, weight or rate of delivery for a measured time interval.

A light emission source 20 issues a beam of light 22 through the transparent conduit sector 16 and through a flow stream of test specimen passing through the transparent sector. Light emerging from the specimen flow steam is received by a photosensor means 24.

Characteristically, the photo sensor 24 generates an electrical signal in response to the magnitude of photon incidence. Hence, the photosensor emission signal fluctuates as a function of the light flow stream. This relationship is exploited to signal the passage of a light obstructing particle. Additionally, the size of the passing particle may also be reported.

Such photosensor 24 signals are transmitted by signal conduit 26 to a central processing unit 28, for example.

Depending on the program objectives, the signals may be processed to count passing particles in distinctive size categories for a particle size distribution data base. Such data may be displayed for human perception by a meter or video monitor 30.

Figure 2:
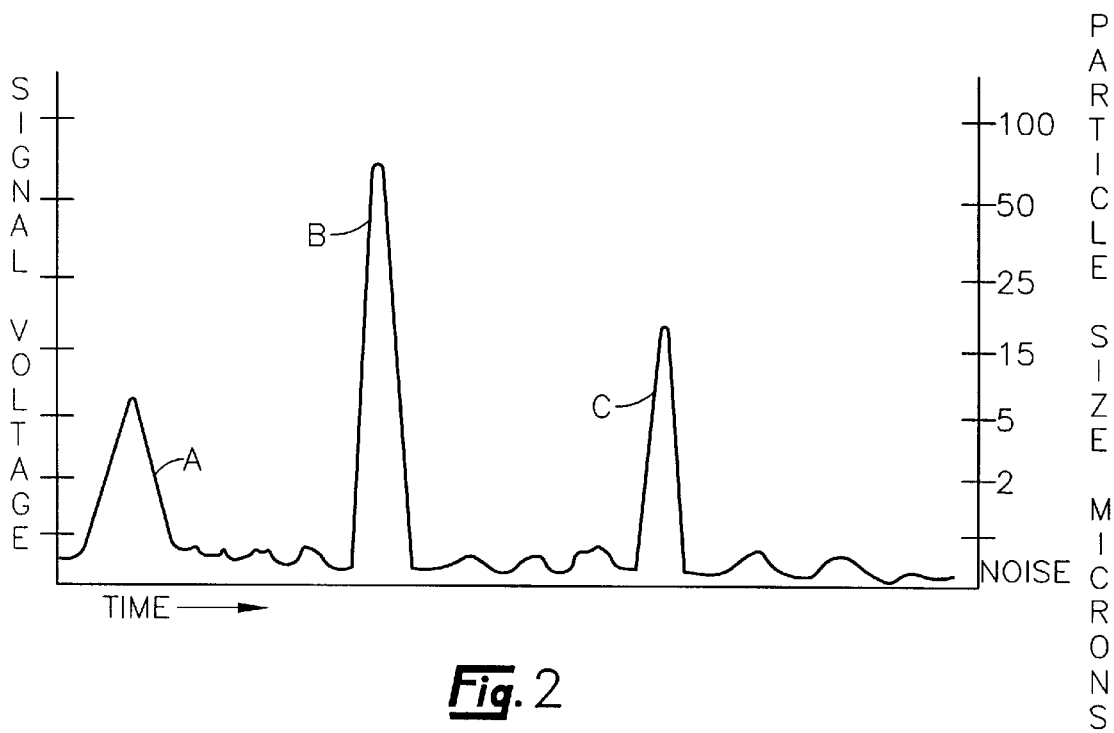
FIG. 2 is a representative signal pattern generated by an optical particle counter.

With respect to FIG. 2, voltage signals generated by a photo diode 24 are graphed as a function of time. Since the signal value has a direct relationship to the particle size, the size value may be appropriately, albeit exponentially, scaled along the same ordinate axis as the signal value. Specifically, voltage spike A may represent the passage of a 5 micron particle. Voltage spike B may represent the passage of a 60 micron particle. Voltage spike C represents an 18 micron particle. When the signal voltage values are charted as a function of time as illustrated by FIG. 2, the signal spike aspect ratio may also be evaluated to appraise the particle shape and/or volume.

Such signal characteristics are compared to predetermined set-point values that define categories of interest. As a test quantity of specimen fluid passes through the transparent sector 16 of the instrument, substantially all of the particles present and passing are accounted for by respective size category. Resultantly, a particle size distributive data base is generated by appropriate programming of the CPU 28.

As previously noted, a specimen of contaminated oil comprising dispersed water may provide an optical particle count that exceeds a count that would correctly be attributable to solid particle contamination. In addition to the "crackle" test and the ASTM D-1744 test for determining the presence of water, we have discovered that a particle size distribution that includes an approximate equality of 2 and 5 micron particles also indicates a strong probability of dispersed water.

In pursuit of a reasonably accurate solid particle count, a water masking solvent is prepared with about one part isopropanol (approx. 0.786 g/ml density) and about three parts toluene (approx. 0.867 g/ml density). Preferably, the solvent mixture is passed through a 0.8 micron or less filter. This water masking solvent is mixed with the contaminated oil test subject at a weight ratio of about 1 part oil and 1 part solvent. This 1:1 mixture constitutes the fluid test specimen for the optical particle count instrument.

Preferably, the water masking solvent is passed through the optical particle counting instrument as an independent fluid specimen prior to mixing with the contaminated oil. This procedure provides a background count data base distinctive to the masking solvent. Clearly, reasonable laboratory cleanliness practices are of significant importance to this procedure for maintenance of a low background contamination. Nevertheless, the background data base for the isolated masking solvent permits segregation of solid particle contamination data that is inadvertently contributed by the masking solvent to the 1:1 test specimen.

Following a first particle count of the water and solid particle contaminated oil specimen prior to mixture with the masking solvent and a second particle count respective to the masking solvent independently, the two are thoroughly mixed. Preferably, the oil and solvent mixture is degassed as in a vacuum chamber to remove air bubbles. A third particle count is obtained from the 1:1 oil and solvent mixture.

Figure 3:
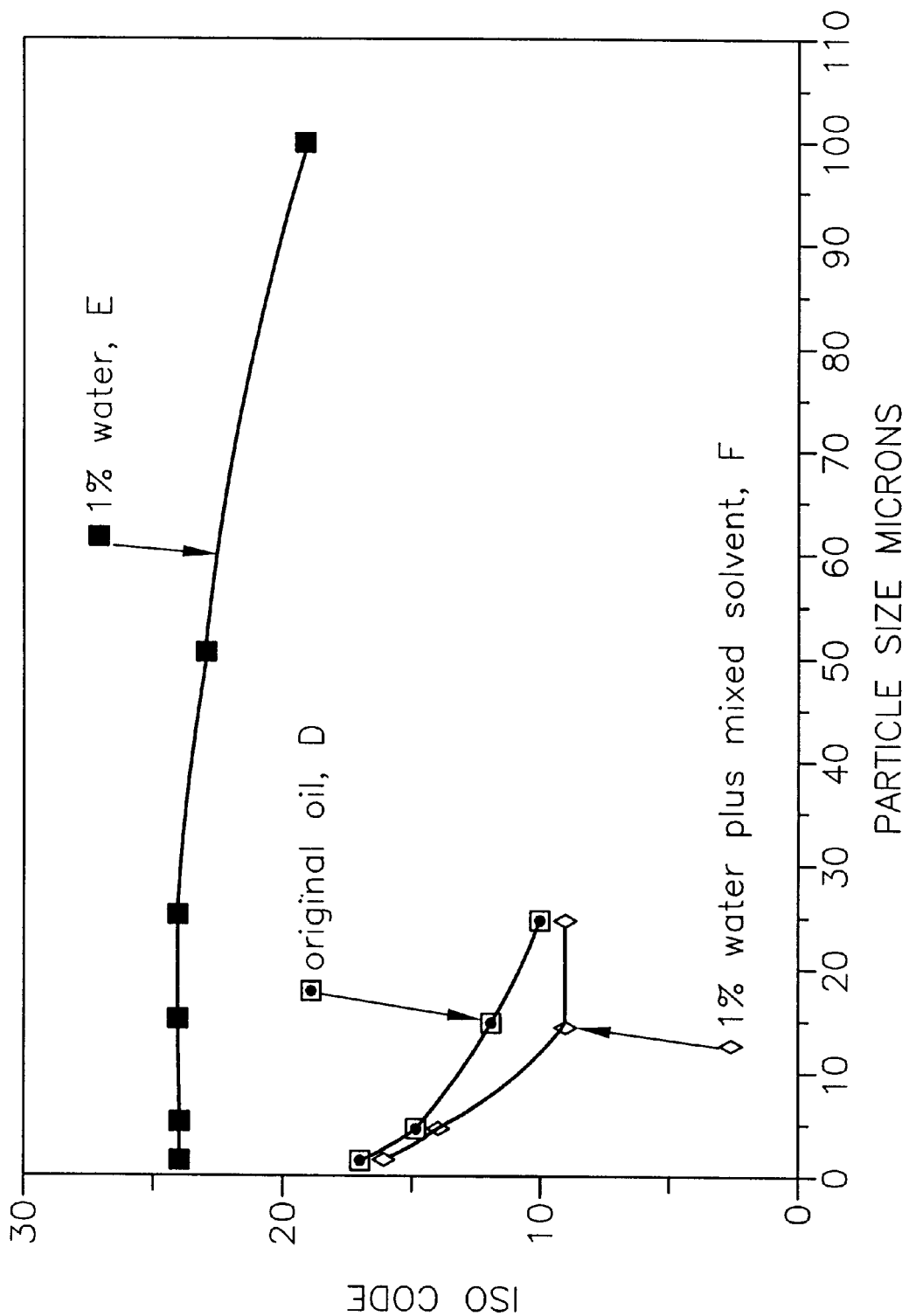
FIG. 3 is a comparative data graph.

A fundamental data correction is obtained from a deduction of the second and third particle counts from the first particle count. This data correction quantifies the solid particle contribution to a combined oil contamination system, independently of the water particle contribution. An example of this relationship is illustrated by the graph of FIG. 3. An original oil sample (graph line D) that had been processed through a laser particle counter was reported to contain a solid particle contamination corresponding to an ISO code cleanliness level of 17 at about 2 microns. The cleanliness level fell to an ISO code cleanliness level of 10 at about 25 microns.

Following acquisition of a particle count data base known to be exclusively solid particles, the original oil sample was further contaminated with 1% (10,000 ppm) water. The laser particle counter report on the oil sample contaminated with both water and solid particles is represented by graph line E. From the line E, it is seen that an ISO cleanliness code of 24 occurred for particles in the 2 micron range and fell to a code of about 10 at 100 microns. Also to be noted is the relative "flatness" of the line E over a wide particle size spectrum. Line E is substantially linear along a slight, negative slope.

This 1% water contaminated oil sample was next mixed about 1:1 (weight) with the masking solvent blend described above as including the weight measured proportions of about 1 part isopropanol (99.7% or better purity) and about 3 parts toluene (99.7% or better purity) and degassed. FIG. 3 graph line F represents the particle size distribution reported for the oil/solvent mixture that is very close to the original oil sample distribution represented by line D.

More particularly, isopropanol (2-propanol) is miscible with water in all proportions. However, the solubility of isopropanol in mineral oil is extremely low. Toluene on the other hand, is soluble in all proportions with mineral oil but is substantially immiscible with water. Nevertheless, because both isopropanol and toluene are small molecule organics, the two are miscible.

Pursuant to the present invention, a solution of 3 parts toluene and 1 part isopropanol is soluble in mineral oil. The isopropanol, carried into solution with the oil by the toluene, consequently enters solution association with water present in the oil. The result is a clear oil solution having a substantially homogenous optical refraction index.

Experimentation has established a preferred weight ratio of about 3 parts toluene to about 1 part isopropanol. Substantially smaller proportions of isopropanol have been found to be insufficient for dissolving the concentrations of water most often found in lubrication or insulation oils. Conversely, a substantially greater proportion of isopropanol tends to segregate from the solution as an emulsion.

It will also be appreciated that in addition to an isolated count of solid particles, a particle distribution survey as represented by graph line E of FIG. 3 may also be used to determine the relative quantity of water present in the contaminated oil sample. Since the solid particle contribution to the total particle count in the contaminated sample, may be isolated, the remainder is presumed to be water. Hence, the particle distribution difference between lines E and F is presumed to represent water sites. Data representing the number of particles respective to a spectrum of particle sizes may be integrated to conclude a total volume sum in the form of distributed water particles. This water volume sum may be translated into a total water weight that may be proportionalized to the total sample weight.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

As our invention, therefore,

We claim:

1. A method of determining the quantity of free immiscible fluid dispersed as droplet particles in the presence of oil having solid particles suspended therein, said method comprising the steps of optically determining the combined particle size distribution of substantially all particles in a sample of said oil, mixing said oil sample with a masking fluid that is soluble with said oil and said immiscible fluid, optically determining the size distribution of substantially all particles remaining in said oil sample after mixing with said masking fluid, and deducting the remaining particle size distribution from the combined particle size distribution to conclude a quantity of free immiscible fluid initially present in said oil sample.

2. A method as described by claim 1 wherein said masking fluid comprises about one part isopropanol and about three parts toluene.

3. A method as described by claim 2 wherein about one part of said oil sample is mixed with about one part of said masking fluid.

4. A method as described by claim 1, wherein the particle size distribution in said sample is determined by laser emission means.

5. A method of operating a photo responsive particle counter having a fluid flow channel through a view volume, a view area of said view volume that is substantially transparent between opposite sides of said view area, light emission means on one side of said view area, light detection means on an opposite side of said view area and particle counting means responsive to signals from said light detection means signifying the passage of light obstructing particles through said view volume, said method comprising the steps of preparing a solvent having about one part isopropanol and about three parts toluene, preparing a test sample by mixing about one part of said solvent with about one part of a test oil having light obstructing particles and substantially immiscible fluids mixed therewith and flowing a measured portion of said test sample through said view volume and counting the number of light obstructing particles mixed therewith.

6. A method of operating a particle counter as described by claim 5 wherein a particle count respective to said solvent is obtained independently of said test oil.

7. A method of operating a particle counter as described by claim 5 wherein the particle count from said test sample is adjusted according to the particle count of said solvent.

8. A method of operating a particle counter as described by claim 5 wherein said light emission means is a laser means.

9. A method of counting substantially solid particulates suspended in a contaminated oil medium having substantially immiscible fluids mixed with solid particles, said method comprising the steps of preparing a solvent comprising about one part isopropanol and about three parts toluene, mixing a test fluid with about one part solvent and about one part of said contaminated oil medium, flowing a predetermined portion of said test fluid through a substantially transparent view volume, and optically counting the number of substantially solid particulates in the predetermined portion of said test fluid.

10. A method as described by claim 9 wherein said one part solvent is caused to flow through said transparent view volume independently of said contaminated oil medium while the number of substantially solid particulates in said solvent is optically counted.

11. A method as described by claim 10 wherein the number of particulates counted from said portion of test fluid is adjusted according to the number of solid particulates counted in said solvent.

12. A method as described by claim 9 wherein a laser light source is directed through said view volume while said test fluid flows therethrough for optically counting said solid particulates.

13. A method of operating a photo responsive particle counter having a fluid flow channel through a view volume, a view area of said view volume that is substantially transparent between opposite sides of said view area, light emission means on one side of said view area, light detection means on an opposite side of said view area and particle counting means responsive to signals from said light detection means signifying the passage of light obstructing particles through said view volume, said method comprising the steps of: preparing a test sample by mixing test oil with a masking solvent, said test oil having dispersed therein light obstructing particles and at least one contamination fluid that is substantially immiscible with said oil, said masking solvent being miscible with said oil and said contamination fluid; and, flowing a measured portion of said test sample through said view volume and counting the number of light obstructing particles mixed therewith.

14. A method of operating a particle counter as described by claim 13 wherein a particle count respective to said solvent is obtained independently of said test oil.

15. A method of operating a particle counter as described by claim 14 wherein the particle count from said test sample is adjusted according to the particle count of said solvent.

16. A method of operating a particle counter as described by claim 13 wherein said light emission means is a laser means.

17. A method of operating a photo responsive particle counter having a fluid flow channel through a view volume, light emission means, light detection means and particle counting means responsive to signals from said light detection means signifying the passage of light obstructing particles through said view volume, said method comprising the steps of: preparing a solvent having about one part isopropanol and about three parts toluene; preparing a count of light obstructing particles dispersed within said solvent; preparing a test sample by mixing about one part of said solvent with about one part of a test oil having light obstructing particles and fluids that are oil immiscible mixed therewith; and, flowing a measured portion of said test sample through said view volume and counting the number of light obstructing particles mixed therewith.

18. A method of operating a particle counter as described by claim 17 wherein the particle count from said test sample is adjusted according to the particle count of said solvent.

19. A method of operating a particle counter as described by claim 17 wherein said light emission means is a laser means.

20. A method of counting substantially solid particulates suspended in a contaminated oil medium having substantially immiscible fluids mixed with solid particles, said method comprising the steps of:

preparing a solvent comprising about one part isopropanol and about three parts toluene; flowing said solvent through a substantially transparent view volume while the number of substantially solid particles disposed within said solvent is optically counted; mixing a test fluid with about one part of said solvent and about one part of said contaminated oil medium; flowing a predetermined portion of said test fluid through said view volume; and, optically counting the number of substantially solid particles in said predetermined portion of said test fluid.

21. A method as described by claim 20 wherein the number of particles counted from said portion of test fluid is adjusted according to the number of solid particles counted in said solvent.

22. A method as described by claim 20 wherein a laser light source is directed through said view volume while said test fluid flows therethrough for optically counting said solid particles.

23. A method of operating a photo responsive particle counter having a fluid flow channel through a view volume, a view area of said view volume that is substantially transparent between opposite sides of said view area, light emission means on one side of said view area, light detection means on an opposite side of said view area and particle counting means responsive to signals from said light detection means signifying the passage of light obstructing particles through said view volume, said method comprising the steps of:

preparing a solvent with known particle count data;

preparing a test sample by mixing said solvent with a known quantity of test oil having light obstructing particles mixed therewith;

flowing a measured portion of said test sample through said view volume; and counting the number of light obstructing particles mixed therewith.

24. A method of operating a particle counter as described by claim 23 wherein said light emission means is a laser means.

* * * * *